United States Patent [19]

Shouldice et al.

[11] Patent Number: 4,715,398
[45] Date of Patent: Dec. 29, 1987

[54] LIQUID LEVEL CONTROL

[75] Inventors: David R. Shouldice, Lakewood; Dennis M. Treu, Morrison, both of Colo.

[73] Assignee: Cobe Laboratories, Inc., Lakewood, Colo.

[21] Appl. No.: 925,818

[22] Filed: Oct. 30, 1986

[51] Int. Cl.$^4$ ............................................. B01D 19/00
[52] U.S. Cl. ...................................... 137/171; 55/219;
   55/189; 55/200; 137/386; 137/624.15
[58] Field of Search ..................... 137/624.13, 624.15,
   137/412, 392, 386, 86, 1, 2, 7, 171; 55/219, 467,
   55, 189, 190, 200

[56] References Cited

U.S. PATENT DOCUMENTS

| | | | |
|---|---|---|---|
| 2,476,104 | 7/1949 | Mason | 137/7 X |
| 3,545,469 | 12/1970 | Cissell | 137/412 X |
| 4,325,347 | 4/1982 | Yamaguchi | 137/487.5 X |
| 4,371,385 | 2/1983 | Johnson | 55/190 |
| 4,597,048 | 6/1986 | Mazur | 137/412 X |

FOREIGN PATENT DOCUMENTS 861157 12/1952 Fed. Rep. of Germany ...... 137/412

Primary Examiner—Alan Cohan

[57] ABSTRACT

Fluid flow apparatus comprising a housing defining a chamber, a chamber inlet and a chamber outlet for the flow of liquid therethrough, a level sensor providing a control signal having a magnitude related to the level of liquid in the chamber, and a valve hydraulically connected to control flow into the inlet or out of the outlet, and controller operably connected to alternately open and close the valve in a duty cycle responsive to the magnitude of the signal.

15 Claims, 1 Drawing Figure

LIQUID LEVEL CONTROL

FIELD OF THE INVENTION

The invention relates to controlling the level of liquid in a fluid flow chamber.

BACKGROUND OF THE INVENTION

It may be desirable to sense and control the level of a liquid flowing through a fluid flow chamber. For example, in a deaeration chamber of dialysate preparation apparatus, if the level of liquid goes below the outlet, air removed from the liquid will be undesirably pumped downstream with the water.

SUMMARY OF THE INVENTION

The invention features in general controlling the flow through a fluid flow chamber by using a level sensor providing a control signal having a magnitude related to the level of the liquid in the chamber and using the signal to control the duty cycle of a valve that is alternately opened and closed to control flow into or out of the chamber.

In preferred embodiments, there is a pump connected to the outlet of the chamber, and the valve is connected to the inlet; the chamber is a deaeration chamber; the controller calculates a desired duty cycle a plurality of times during each period of the duty cycle and compares the desired duty cycle with the proportion of time that the valve has been opened in the period and closes the valve if the desired duty cycle equals or is smaller than the proportion, and the controller sets the duty cycle by calculating the difference between the actual level and a commanded level, the integral of the difference, and the sum of constants times these values; and a heater is turned off if the duty cycle is 100%, if the liquid goes below a minimum level for greater than 20 seconds or if a flow switch indicates that there has been no flow for 10 seconds or more.

Other advantages and features of the invention will be apparent from the following description of the preferred embodiment thereof and from the claims.

DESCRIPTION OF THE PREFERRED EMBODIMENT

Figure 1:
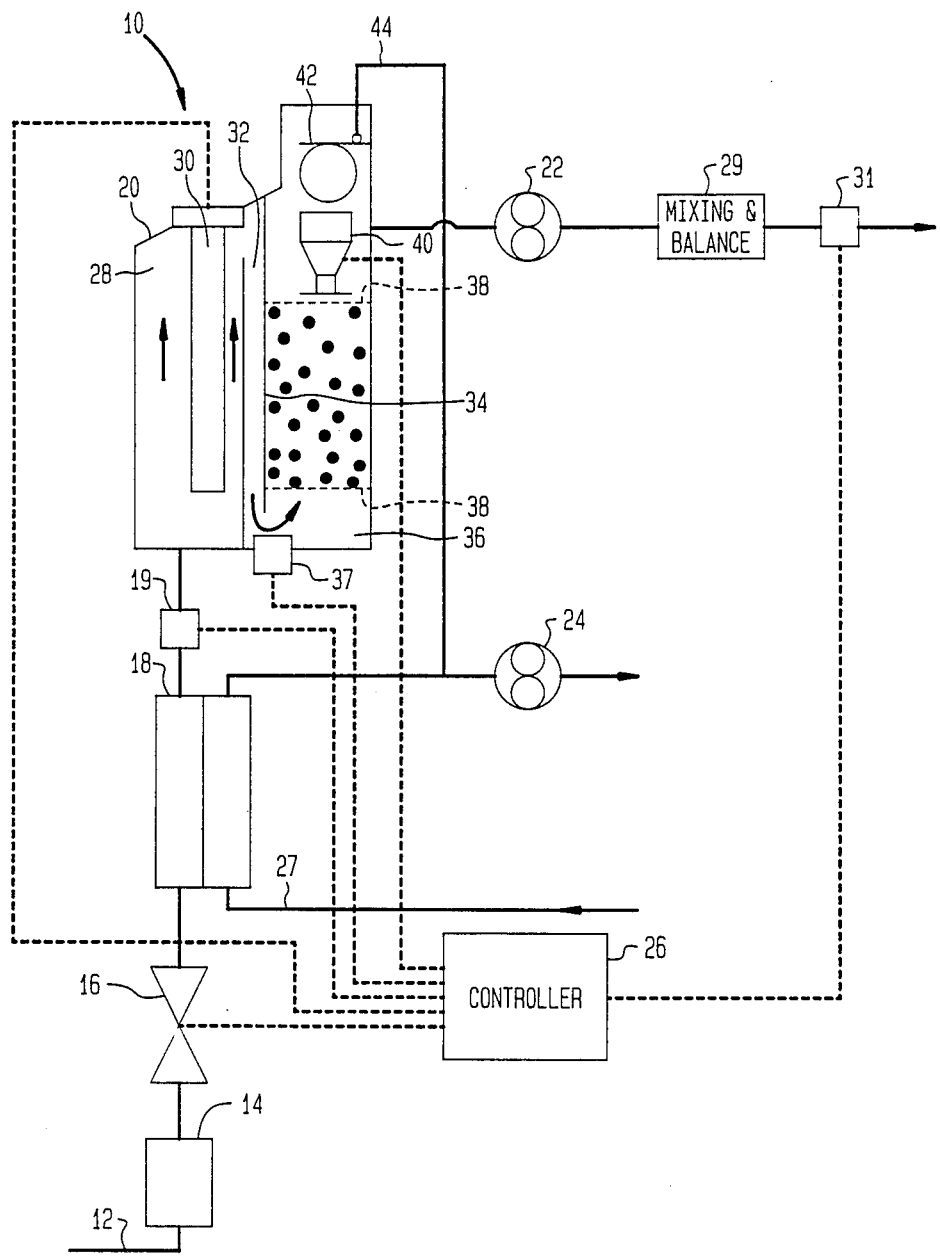
Figure 1:
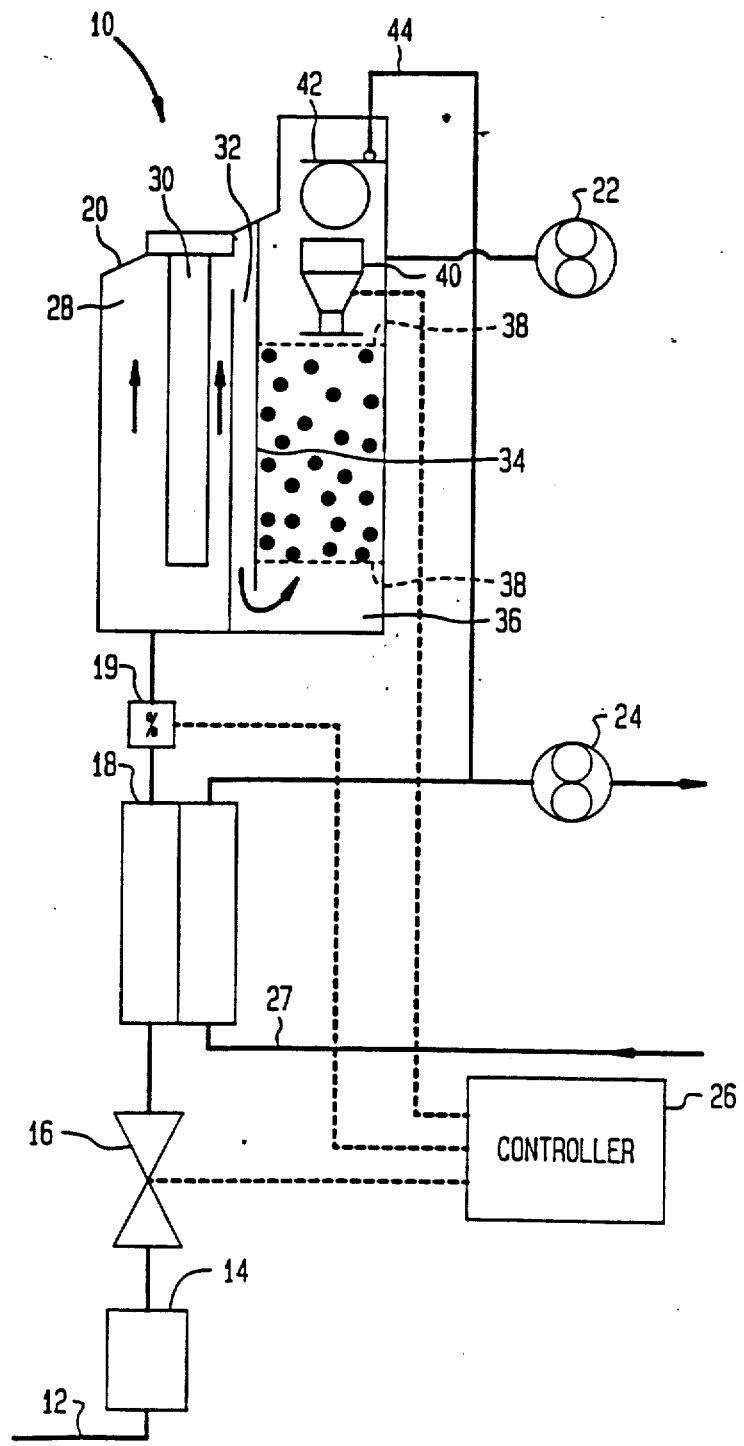

The preferred embodiment will now be described.
Drawing

The drawing is a diagrammatic representation of a deaeration portion of a dialysate preparation machine.
Structure Referring to the drawing, there is shown apparatus 10 for deaerating water used in a dialysate preparation and supply machine of the type shown in Johnson U.S. Pat. No. 4,371,385. It includes inlet 12 for receiving tap water, inlet pressure regulator 14 (adjusted to have an outlet pressure of 6 psi when its outlet is not connected to a further pressure reducer), two-position (open-closed) solenoid valve 16, heat exchanger 18, flow sensing switch 19, heater/deaerator 20, deaeration pump 22, vacuum/waste pump 24, and electronic controller 26, connected to receive signals from level sensor 40 and to control valve 16 and control other components (not shown) of the dialysate preparation machine. Pumps 22, 24 are positive displacement gear pumps. Controller 26 is programmed to include a PID controller, which uses the level sensing information from sensor 40 in controlling the duty cycle of valve 16.

Heater/deaerator 20 includes tubular flow passage 28, which surrounds heater 30 and overflows into passage 32 on the left side of baffle 34 between the heating zone in passage 28 and deaeration chamber 36. Deaeration chamber 36 includes polypropylene particles (spheres and cylinders approximately 0.090" in diameter) that are prevented from flowing beyond screens 38 located below level sensor 40 (including a Hall effect magnetic position sensor in a fixed vertical guide rod that senses the position of magnets in a float that is vertically slidably mounted on the guide rod). At the top of deaeration chamber 36 is bleed valve 42 blocking flow of liquid through gas outlet 44 connected to vacuum/waste pump 24.

Operation

Water entering from inlet 12 passes through pressure regulator 14, which provides protection from large line pressure variations, and solenoid valve 16, which is alternately opened and closed and has a 6-second period. The duty cycle of valve 16 is controlled by controller 26 so as to be open a portion of the 6-second period depending upon the liquid level indicated by the output voltage from level sensor 40, as is described in detail below.

Water flows through heat exchanger 18, receiving heat from the spent dialysate, and enters heating passage 28, flows upward in it, spills over into passage 32 and flows under baffle 34 into deaeration chamber 36. The liquid in heater/deaerator 20 is subjected to negative pressure by deaeration pump 22 and by vacuum pump 24. Pump 22 is operated at a fixed voltage to pump at a constant rate (the value of which can be adjusted by the operator), and pump 24 is operated to pull on the air in chamber 36 to maximize the vacuum in chamber 36, without overpowering pump 22. The negative pressure and increased temperature cause volatilization of dissolved gas from the liquid. Plastic particles between screens 38 provide nucleation sites at which air bubbles form. Gas accumulating above the liquid surface passes through valve 44 and pump 24 while average liquid level is maintained constant by level sensor 40 and controller 26.

Controller 26 samples the voltage of sensor 40, indicating actual instantaneous level in chamber 36, a plurality of times a minute and employs the PID controller (involving a proportional, integral and derivative calculation, according to procedures well known in the art, e.g., as disclosed in Kuo, *Digital Control Systems*, Holt, Rinehart & Winston, 1980 pp. 509–514, which is hereby incorporated by reference) to control the duty cycle.

Each time that a sample is taken, controller 26 determines the difference between the actual level (AL) and commanded level (CL), which might best be thought of as a desired overall average level toward which the controller aims. The duty cycle D at time i is then calculated using the following formula:

$$D = K_p \times (AL - CL) + K_d \times d(AL - CL)/dt + K_i \times \int_{t_0}^{t_i} (AL - CL)$$

where:

$K_p$ and $K_i$ are the empirically determined gain values for the proportional and integral terms, and $K_d$ is the gain value for the derivative term, set equal to zero in the preferred embodiment.

This calculation is performed after each sample. If at some point during the open portion of the six-second period the proportion of time into the six-second period is equal to or greater than the calculated duty cycle D, the valve 16 is closed. The integrated portion of the calculation is related to the long-term average, and the proportional portion is related to the actual level. The use of the integrated portion avoids phase lag oscillation that might otherwise result from using the proportional portion of the calculation alone.

If the actual level goes below a minimum value for more than 20 seconds, if the duty cycle is 100% or if flow switch 19 indicates that there has been no flow through it for 10 seconds, heater 30 is turned off to avoid damage to it.

Deaerated water supplied by pump 22 to the remainder of the hydraulic circuitry of the dialysate preparation machine is mixed with dialysate concentrate and provided to the dialysate side of a dialyzer. Spent dialysate returns from the dialyzer to inlet 27 of heat exchanger 18, and is removed via vacuum/waste pump 24.

OTHER EMBODIMENTS

Other embodiments of the invention are within the scope of the following claims.

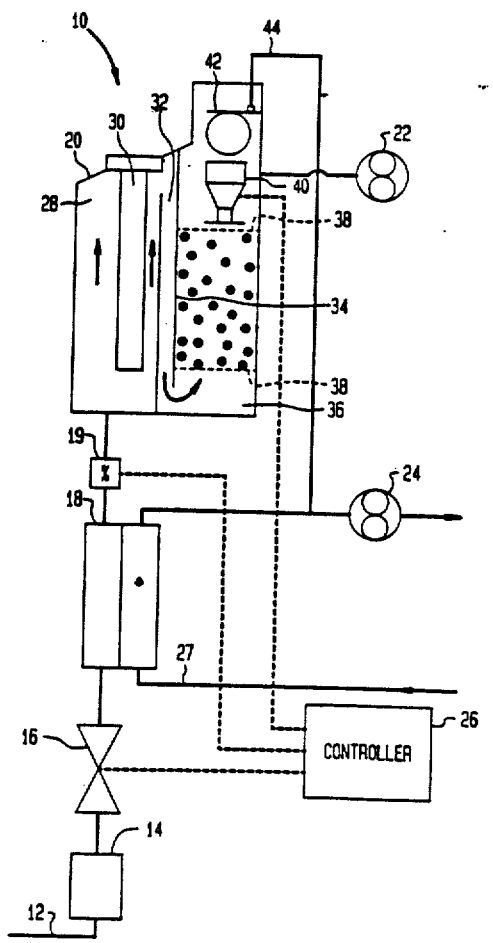

What is claimed is:

1. Fluid flow apparatus comprising
   a housing defining a deaeration chamber, a chamber inlet and a chamber outlet for the flow of liquid therethrough,
   said housing having a gas outlet at its top for the removal of gas volatilized from said liquid,
   a level sensor providing a control signal having a magnitude related to the level of liquid in said chamber,
   a valve hydraulically connected to said chamber inlet to control flow into said inlet,
   a pump connected to said chamber outlet,
   a source of negative pressure connected to said gas outlet, and
   a controller operably connected to alternately open and close said valve in a duty cycle responsive to the magnitude of said signal.

2. Fluid flow apparatus comprising
   a housing defining a chamber, a chamber inlet and a chamber outlet for the flow of liquid therethrough,
   a level sensor providing a control signal having a magnitude related to the level of liquid in said chamber,
   a valve hydraulically connected to control flow into said inlet or out of said outlet, and
   a controller operably connected to alternately open and close said valve in a duty cycle responsive to the magnitude of said signal,
   wherein said controller calculates a desired duty cycle a plurality of times during each period of the duty cycle.

3. The apparatus of claim 2 wherein a pump is connected to said outlet, and said valve is connected to said inlet.

4. The apparatus of claim 3 wherein said chamber is a deaeration chamber, and said housing has a gas outlet at its top for the removal of gas volatilized from said liquid.

5. The apparatus of claim 2 wherein said controller compares the desired duty cycle with the proportion of time that the valve has been open during the period, and closes the valve if the desired duty cycle equals or is smaller than said proportion.

6. The apparatus of claim 2 wherein said controller sets said desired duty cycle by calculating the difference between the actual level in said chamber and a commanded level.

7. The apparatus of claim 6 wherein said controller calculates the integral of said difference in setting said duty cycle.

8. The apparatus of claim 7 wherein said controller calculates the sum of a constant times said difference and a constant times said integral.

9. Fluid flow apparatus comprising
   a housing defining a chamber, a chamber inlet and a chamber outlet for the flow of liquid therethrough,
   a level sensor providing a control signal having a magnitude related to the level of liquid in said chamber,
   a valve hydraulically connected to control flow into said inlet or out of said outlet,
   a controller operably connected to alternately open and close said valve in a duty cycle responsive to the magnitude of said signal, and
   a heater upstream of said chamber,
   said controller being operative to deactivate said heater upon the occurrence of a particular flow condition.

10. The apparatus of claim 9 wherein a said particular flow condition is indicated by a 100% duty cycle.

11. The apparatus of claim 9 wherein a said particular flow condition is a level below a minimum threshold for greater than a predetermined period of time.

12. The apparatus of claim 10 further comprising a flow switch indicating flow through said chamber, and wherein a said particular condition is no flow through said flow switch.

13. Dialysate preparation apparatus comprising
    a housing defining a deaeration chamber, a chamber inlet and a chamber outlet for the flow of liquid therethrough,
    said housing having a gas outlet at its top for removal of gas volatilized from said liquid,
    a level sensor providing a control signal having a magnitude related to the level of liquid in said chamber,
    a valve hydraulically connected to said chamber inlet to control flow into said inlet,
    a pump connected to said chamber outlet,
    a source of negative pressure connected to said gas outlet, and
    a controller operably connected to alternately open and close said valve in a duty cycle responsive to the magnitude of said signal.

14. The apparatus of claim 9 wherein a pump is connected to said outlet, and said valve is connected to said inlet.

15. The apparatus of claim 14 wherein said chamber is a deaeration chamber, and said housing has a gas outlet at its top for the removal of gas volatilized from said liquid.

* * * * *

UNITED STATES PATENT AND TRADEMARK OFFICE
CERTIFICATE OF CORRECTION

PATENT NO.   : 4,715,398

DATED        : December 29, 1987

INVENTOR(S)  : David R. Shouldice et al.

It is certified that error appears in the above-identified patent and that said Letters Patent is hereby corrected as shown below:

The title page showing the illustrative figure should be deleted to appear as per attached title page.
Sheet 1 of the drawing should appear as shown on the attached sheet.

Signed and Sealed this

Sixteenth Day of August, 1988

Attest:

DONALD J. QUIGG

Attesting Officer     Commissioner of Patents and Trademarks

United States Patent [19]

Shouldice et al.

[11] Patent Number: 4,715,398

[45] Date of Patent: Dec. 29, 1987

[54] LIQUID LEVEL CONTROL

[75] Inventors: David R. Shouldice, Lakewood; Dennis M. Treu, Morrison, both of Colo.

[73] Assignee: Cobe Laboratories, Inc., Lakewood, Colo.

[21] Appl. No.: 925,818

[22] Filed: Oct. 30, 1986

[51] Int. Cl.⁴ ............................................. B01D 19/00
[52] U.S. Cl. ................................... 137/171; 55/219; 55/189; 55/200; 137/386; 137/624.15
[58] Field of Search .............. 137/624.13, 624.15, 137/412, 392, 386, 86, 1, 2, 7, 171; 55/219, 467, 55, 189, 190, 200

[56] References Cited

U.S. PATENT DOCUMENTS

| | | | |
|---|---|---|---|
| 2,476,104 | 7/1949 | Mason | 137/7 X |
| 3,545,469 | 12/1970 | Cissell | 137/412 X |
| 4,325,347 | 4/1982 | Yamaguchi | 137/487.5 X |
| 4,371,385 | 2/1983 | Johnson | 55/190 |
| 4,597,048 | 6/1986 | Mazur | 137/412 X |

FOREIGN PATENT DOCUMENTS 861157 12/1952 Fed. Rep. of Germany ...... 137/412

Primary Examiner—Alan Cohan

[57] ABSTRACT

Fluid flow apparatus comprising a housing defining a chamber, a chamber inlet and a chamber outlet for the flow of liquid therethrough, a level sensor providing a control signal having a magnitude related to the level of liquid in the chamber, and a valve hydraulically connected to control flow into the inlet or out of the outlet, and controller operably connected to alternately open and close the valve in a duty cycle responsive to the magnitude of the signal.

15 Claims, 1 Drawing Figure